United States Patent [19]
Boensch et al.

[11] Patent Number: 6,087,139
[45] Date of Patent: *Jul. 11, 2000

[54] PROCESS FOR PRODUCING CITRIC ACID AND/OR CITRATES

[75] Inventors: Rudolf Boensch, Nackenheim; Klaus Hohmann, Hofheim; Juergen Kuhn, Frankfurt am Main, all of Germany; Vaclav Cerny, Kaznejov, Czechoslovakia; Frantisek Hotek, Petrohrad, Czechoslovakia; Jiri Pendl, Pilzen, Czechoslovakia

[73] Assignee: Metallgesellschaft Aktiengesellschaft, Frankfurt am Main, Germany

[*] Notice: This patent issued on a continued prosecution application filed under 37 CFR 1.53(d), and is subject to the twenty year patent term provisions of 35 U.S.C. 154(a)(2).

[21] Appl. No.: 09/176,647

[22] Filed: Oct. 22, 1998

[30] Foreign Application Priority Data

Oct. 30, 1997 [DE] Germany ............................ 197 47 902

[51] Int. Cl.$^7$ ...................................................... C12P 7/48
[52] U.S. Cl. .......................... 435/144; 435/136; 435/803; 435/917
[58] Field of Search ..................................... 435/144, 803, 435/917, 136

[56] References Cited

U.S. PATENT DOCUMENTS

| | | | |
|---|---|---|---|
| 4,851,573 | 7/1989 | Kulprathipanja et al. | 562/580 |
| 4,851,574 | 7/1989 | Kulprathipanja | 562/580 |
| 4,855,494 | 8/1989 | Margureanu et al. | 562/580 |
| 4,924,027 | 5/1990 | Kulprathipanja et al. | 562/580 |
| 5,237,098 | 8/1993 | Bemish et al. | 562/584 |
| 5,759,826 | 6/1998 | Ahlers et al. | 435/144 |

FOREIGN PATENT DOCUMENTS

| | | |
|---|---|---|
| 0 151 470 | 8/1985 | European Pat. Off. |
| 203 533 | 10/1983 | German Dem. Rep. |
| 29 31 759 | 2/1981 | Germany. |
| 19545303C1 | 4/1997 | Germany. |
| 97/10350 | 3/1997 | WIPO. |

*Primary Examiner*—Jon P. Weber
*Attorney, Agent, or Firm*—Herbert Dubno; Jonathan Myers

[57] ABSTRACT

Citric acid and/or the salts thereof are produced from a raw material containing carbohydrates. An aqueous solution of the raw material is converted into a first solution containing citric acid by means of fermentation, and from the first solution a second solution containing citric acid is obtained by means of a cell separation. The second solution is subjected to a protein precipitation at temperatures of 2 to 70° C., and protein is separated by filtration. From the filtration, a third solution containing citric acid is obtained, and the same is passed through a first anion exchanger. The solution containing citric acid, which is discharged from the first anion exchanger, is passed through a second anion exchanger, which is selectively charged with citric acid. The second anion exchanger charged with citric acid is eluted with hydroxide solution or water, and there is thus obtained a fourth solution, in which citrate or citric acid is dissolved. Water is at least partly removed from the fourth solution.

5 Claims, 1 Drawing Sheet

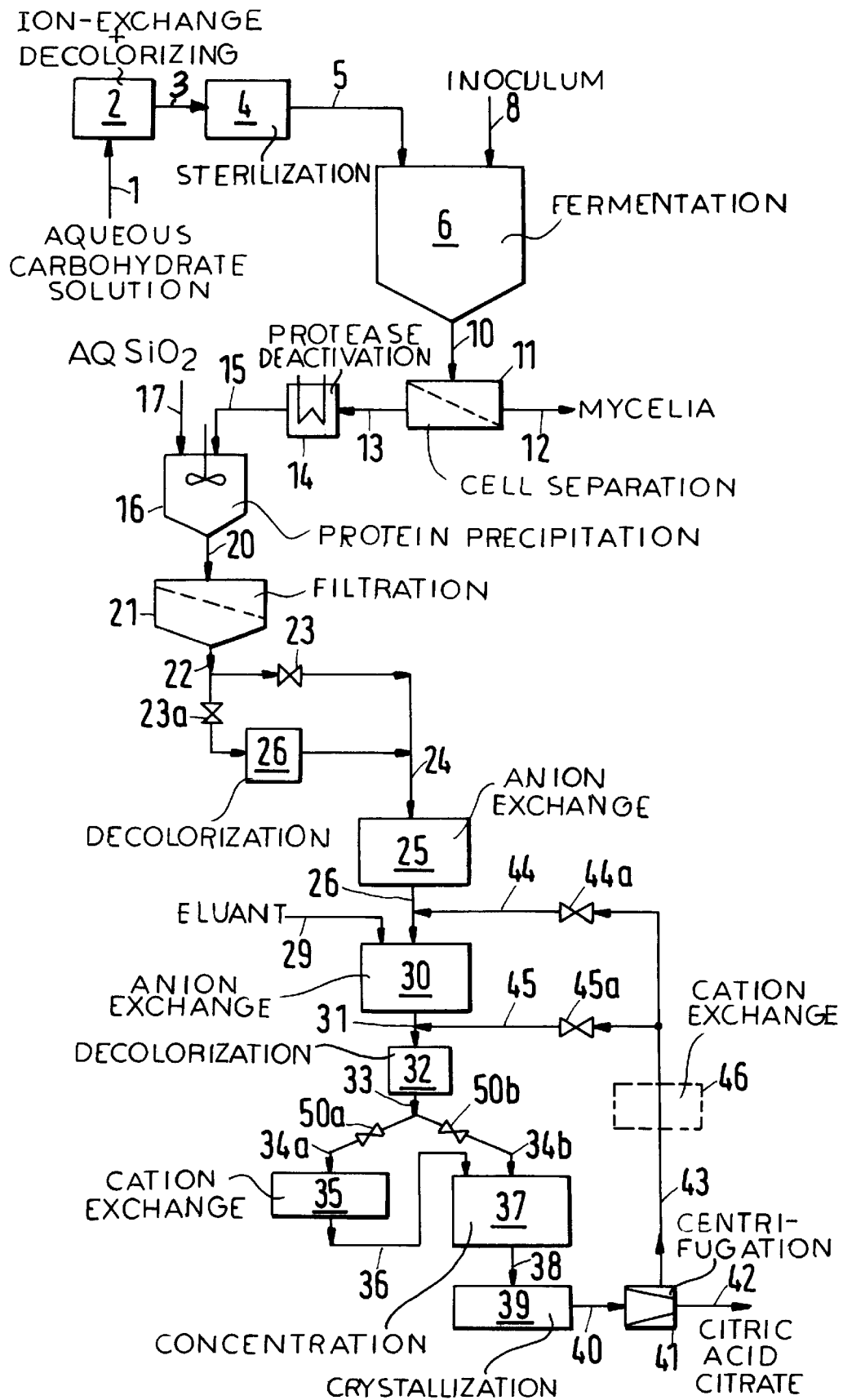

PROCESS FOR PRODUCING CITRIC ACID AND/OR CITRATES

FIELD OF THE INVENTION

Our present invention relates to a process for producing citric acid and/or the salts thereof from a raw material containing carbohydrates, wherein the raw material is purified, an aqueous solution of the raw material is converted into a first solution containing citric acid by fermentation, the first solution is passed through a cell separation and a second solution containing citric acid is obtained, the second solution is subjected to a protein precipitation at temperatures of 2 to 70° C., and the protein is separated by filtration.

BACKGROUND OF THE INVENTION

A process in which citric acid is generated by fermentation is known from DE 195 45 303 C1. This patent describes the production of an organic acid and/or the salts thereof, and in particular the production of lactic acid, citric acid or gluconic acid. The residue of the protein precipitation is recirculated to the cell separation, and in concentrating the product through crystallization, there is also obtained a mother liquor which is recirculated to the protein precipitation.

OBJECT OF THE INVENTION

It is an object of the invention to simplify the known process, to adjust it to the production of citric acid and/or citrate, and to enable production of a largely pure product as inexpensively as possible.

SUMMARY OF THE INVENTION

In accordance with the invention this object is attained in the above-mentioned process by obtaining from the filtration a third solution containing citric acid, and passing the third solution through a first anion exchanger. The solution containing citric acid, which is discharged from the first anion exchanger, is passed through a second anion exchanger which is selectively charged with citric acid. The second anion exchanger charged with citric acid is eluted with hydroxide solution or water, and a fourth solution is obtained, in which the citrate or citric acid is dissolved. Water is at least partly removed from the fourth solution. In this relatively easy way, largely pure citrate and/or citric acid is produced.

A process according to the invention for producing the product which is selected from the group consisting of citric acid and salts thereof, namely, citrate salts, can thus comprise the steps of:

(a) fermenting a raw material containing carbohydrates under fermentation conditions producing the product in a fermentation medium, thereby obtaining a first solution;

(b) subjecting the first solution to cell separation to obtain a second solution containing citric acid;

(c) precipitating protein from the second solution at a temperature of 2° to 70° C. and filtering out precipitated protein to obtain a third solution containing citric acid;

(d) passing the third solution containing citric acid through a first anion exchanger and then passing a solution resulting from passage through the first anion exchanger to anion exchange in a second anion exchanger, thereby selectively charging the second anion exchanger with citric acid;

(e) eluting the second anion exchanger with an eluant selected from the group which consists of water or aqueous hydroxide solution to produce a fourth solution containing the product in solution; and (f) at least partly removing water from the fourth solution to yield the product.

Preferably by eluting the second anion exchanger with hydroxide, the fourth solution containing citrate is obtained, which is decolorized, and from which cations are removed for instance in a cation exchanger and citric acid is obtained before water is at least partly separated from the fourth solution. On the other hand, when water and preferably hot water is employed for eluting the second anion exchanger, a citric acid solution is obtained.

It is advantageous to charge the first anion exchanger with citric acid in the initial state, so as to further increase the purity of the solution discharged from this anion exchanger. Furthermore, the solution having a pH value of 5 to 9 and preferably 6 to 8, which comes from the second anion exchanger, is passed in and through a fixed bed of granular activated carbon in which the solution is decolorized. The activated carbon is in particular used for the removal of sugar.

BRIEF DESCRIPTION OF THE DRAWING

The above and other objects, features, and advantages will become more readily apparent from the following description, reference being made to the accompanying drawing, the sole FIGURE of which is a flow diagram of the process according to the invention.

SPECIFIC DESCRIPTION

As the starting material, an aqueous glucose, sucrose or starch solution is used. We can use, for instance, enzymatically liquefied starch, dilute glucose syrup or dissolved crystalline glucose or sucrose. The solution is supplied via line 1 and first of all subjected to a purification 2. The purification may include an activated-carbon column for decolorizing and in addition a cation and/or anion exchanger. Through line 3, the purified solution is subjected to a continuous sterilization 4 or pasteurization. Via line 5, the sugar or starch solution is then charged into a fermentation 6, where it may in addition be advantageous to add fermentation aids known per se. The liquid in the fermentation 6 is inoculated with fungus spores (*Aspergillus niger*), which are supplied via line 8. The fermentation may be effected in one stage or in several stages.

From the fermentation a first solution is obtained, which is supplied via line 10 to a cell separation 11, where the mycelia are for instance separated by means of a vacuum band filter or by means of centrifugation and are removed via line 12. The largely cell-free solution, here referred to as "second solution", is withdrawn via line 13 and delivered to the deactivation of fungus-specific proteases by means of a brief heat treatment 14. The solution is usually maintained at about 75° C. for 1 to 5 minutes.

The second solution thus treated is delivered through line 15 to a protein precipitation 16. The solution of line 15 usually contains 10 to 25 wt-% citric acid, and in addition to other dissolved organic and inorganic constituents also contains a small amount of cellular debris.

In the protein precipitation 16 it is advantageous to mix the solution in the batch operation with an aqueous $SiO_2$ solution, which comes from line 17. There is for instance used SiO$_2$ with a BET surface of 300 to 500 m$^2$/g, where the solution of line 17 contains 20 to 40 wt-% SiO$_2$. Per m$^3$ of solution supplied via line 15, an amount of 0.1 to 10 l SiO$_2$ solution is usually added as precipitation aid through line 17. The protein precipitation is preferably carried out at temperatures in the range from 40 to 60° C. After reaction times of 0.5 to 4 hours, the suspension produced is supplied via line 20 to a filtration means 21.

The filtration means 21 preferably operates in several stages and also includes an ultrafiltration for removing residual proteins. A purified solution, here also referred to as the "third solution", is withdrawn via line 22, and through the opened valve 23 in line 24 may be supplied directly to a first anion exchanger 25. Instead, it may however be advantageous to first of all pass the third solution through the opened valve 23a through a decolorization 26, before it is charged into the first anion exchanger 25. For the decolorization an activated-carbon fixed bed can be used.

The first anion exchanger 25 is chiefly used for separating inorganic anions from the third solution containing citric acid. The anion-exchange material can in the initial state be charged with citric acid. During the passage of the third solution, this citric acid is at least partly released to the solution, so that the purity thereof is further increased. The solution discharged from the first anion exchanger via line 26 is passed through a second anion exchanger 30. In the second anion exchanger 30 the dissolved citric acid is bound selectively, whereas disturbing cations and residual sugar as well as amino acids are not bound and leave the second anion exchanger via a line not shown in the drawing. The second anion exchanger 30 may for instance be present in the OH form or contain free ammonium groups, so as to be able to bind citric acid.

When the second anion exchanger 30 is fully charged with citric acid, the same is eluted in a separate process step. For eluting purposes, a hydroxide solution or even water may be used, where the elution liquid is supplied through line 29. When the elution liquid contains NaOH, sodium citrate is dissolved in the outflow of line 31. The solution in line 31 is also referred to as the "fourth solution". When eluting with water, the fourth solution is free from sodium and contains citric acid.

The fourth solution in line 31 is first of all passed through a decolorization 32 (e.g. activated carbon) and is obtained as decolorized solution in line 33. When the solution contains anions, e.g. Na$^+$, which would be disturbing in the product, the solution is supplied through the opened valve 50a and line 34a to a cation exchanger 35, which is binding these anions. Instead of the cation exchanger 35 there may also be used an electrodialysis. Subsequently, the solution is delivered through line 36 to a concentration and evaporation 37. But when the fourth solution in line 33 contains no disturbing anions, or citrate should be obtained as product, the solution is supplied through the opened valve 50b and line 34b directly to the concentration and evaporation 37. Concentrated liquid is withdrawn via line 38 and delivered to a crystallization 39.

The crystal-containing suspension obtained is delivered via line 40 to a centrifuge 41, from which the product, citric acid or citrate in a pure, crystalline form, is withdrawn via line 42. The mother liquor is discharged via line 43 and delivered either through the opened valve 44a and line 44 to the second anion exchanger 30 or through the opened valve 45a and line 45 to the decolorization 32.

If necessary, the liquid in line 43 is also passed through a cation exchanger 46, so as to achieve a higher purity.

EXAMPLE

Using a flow scheme corresponding to the drawing, in which the valves 23a, 50a and 44a are closed, sodium citrate of pharmaceutical quality is produced. The purified and sterilized sugar solution is delivered through line 5 to the fermentation 6. The solution consists of 1.2 t sugar, which are dissolved in 5.9 t water. There is employed a bubble column fermenter, and the temperature is 32° C. 100 g fungus spores *Aspergillus nigar* are added to the fermenter; the fermentation is performed for 5 days with aeration.

The subsequent cell separation 11 is effected by means of a vacuum band filter, and during the short-time heat treatment 14 the second solution is maintained at 80° C. for 7 minutes. Per liter, the solution in line 15 contains 0.5 g sugar, 200 g citric acid, 5 g dissolved proteins, 2.4 g cations and 2.5 g anions. Per m$^3$ solution in line 15, 0.5 l SiO$_2$ solution are added in the protein precipitation 16, which SiO$_2$ solution contains 70 wt-% SiO$_2$ colloidally dissolved in water.

Upon briefly stirring the solutions from lines 15 to 17, the suspension formed in the precipitation 16 is allowed five hours residence time for depositing the protein sludge, which is then recirculated as filtration aid to the cell separation 11.

The largely clear liquid containing citric acid is passed through line 20 to the ultrafiltration 21, where residual protein is removed. Through the opened valve 23, the filtered liquid is delivered to the first anion exchanger 25, which in the initial state is charged with citric acid, and then to the second anion exchanger 30, which is in the OH form. For both exchangers, 5 m$^3$ Lewatit (Bayer) is used. The elution liquid in line 29 is an aqueous NaOH solution with 10 wt-% NaOH. The fourth solution withdrawn via line 31 contains 170 g/l trisodium citrate as well as trace amounts of sugar and organic impurities, the pH value is 7.5.

The decolorization 32 employs a fixed bed of activated carbon (EPIBON of Lurgi) with a volume of 5 m$^3$. Through line 34b, the solution is supplied to the concentration and evaporation 37, which employs circulation evaporators. The solution in line 38, which leads to the continuously operating crystallizer 39, contains 960 g/l trisodium citrate, and the suspension in line 40 contains 1200 g/l trisodium citrate.

The mother liquor is recirculated through line 43 without the cation exchanger 46 through the opened valve 45a and through line 45 to the decolorization 32.

We claim:

1. A process for producing a product selected from the group which consists of citric acid and citrate salts, comprising the steps of:

(a) fermenting a raw material containing carbohydrates under fermentation conditions producing said product in a fermentation medium, thereby obtaining a first solution containing citric acid;

(b) subjecting said first solution to cell separation to obtain a second solution containing citric acid;

(c) precipitating protein from said second solution at a temperature of 2° to 70° C. and filtering out precipitated protein to obtain a third solution containing citric acid;

(d) passing said third solution containing citric acid through a first anion exchanger, said first anion exchanger being charged with citric acid before passage of said third solution to separate inorganic anions from said third solution, and then passing a solution containing citric acid resulting from passage of the third solution through the first anion exchanger to anion exchange in a second anion exchanger, thereby selectively charging the second anion exchanger with citric acid;

(e) eluting said second anion exchanger with an eluant selected from the group which consists of water or aqueous hydroxide solution to produce a fourth solution containing the citric acid or citric acid salts in solution; and (f) at least partly removing water from said fourth solution to yield said citric acid or citric acid salts.

2. The process defined in claim 1 wherein the second anion exchanger is eluted with an aqueous hydroxide solution and the resulting fourth solution, which contains citrate, is subjected to decolorization and removal of cations to form citric acid in said fourth solution before water is at least partially removed in step (f).

3. The process defined in claim 2 wherein said third solution, following filtering of precipitated protein is subjected to decolorization before being passed to said first anion exchanger.

4. The process defined in claim 1 wherein said third solution, following filtering of precipitated protein is subjected to decolorization before being passed to said first anion exchanger.

5. The process defined in claim 1 wherein the solution eluted from said second anion exchanger is introduced in a fixed bed of granular activated carbon to be decolorized therein.

* * * * *